(12) United States Patent
Eng

(10) Patent No.: US 6,887,953 B2
(45) Date of Patent: May 3, 2005

(54) ESTERIFICATION PROCESS

(75) Inventor: John Harvey Eng, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 249 days.

(21) Appl. No.: 10/269,734

(22) Filed: Oct. 11, 2002

(65) Prior Publication Data

US 2004/0072983 A1 Apr. 15, 2004

(51) Int. Cl.$^7$ .................................................. C08F 2/00
(52) U.S. Cl. ..................... 526/67; 528/302; 528/308.6; 528/481; 528/501; 528/503; 526/65; 526/66; 526/68
(58) Field of Search .............................. 528/302, 308.6, 528/481, 501, 503; 526/65, 66, 68

(56) References Cited

U.S. PATENT DOCUMENTS

| | | |
|---|---|---|
| 3,496,146 A | 2/1970 | Mellichamp |
| 3,927,982 A | 12/1975 | Chapman et al. |
| 4,680,376 A | 7/1987 | Heinze et al. |
| 5,015,759 A | 5/1991 | Lowe |
| 5,340,909 A | 8/1994 | Doerr et al. |
| 5,798,433 A | 8/1998 | Schmidt et al. |
| 6,277,947 B1 | 8/2001 | Kelsey et al. |
| 6,326,456 B2 | 12/2001 | Kelsey et al. |

*Primary Examiner*—Samuel A. Acquah

(57) ABSTRACT

A process that can be used for direct esterification of a dicarboxylic acid such as terephthalic acid with a glycol such as 1,3-propanediol. The process comprises (1) contacting, at an elevated temperature, optionally in the presence of a preformed oligomer, the acid with the glycol to produce a product mixture comprising (i) a water-glycol vapor mixture, which or a portion of which exits the product mixture at the temperature to form a water-glycol vapor mixture and (ii) a liquid product mixture comprising an oligomer having a degree of polymerization of from about 1.9 to about 3.5 and comprising repeat units derived from the acid; (2) separating the glycol from the water-glycol mixture to produce a recovered glycol; and (3) returning the recovered glycol to the product mixture such that the liquid product mixture comprises an excess free glycol.

24 Claims, No Drawings

ESTERIFICATION PROCESS

FIELD OF THE INVENTION

The present invention provides a process for the esterification of terephthalic acid with 1,3-propanediol to produce an oligomer and a process for using the oligomer in a polymerization process for the production of high molecular weight polytrimethylene terephthalate.

BACKGROUND OF THE INVENTION

Commercial processes for preparing polyalkylene terephthalates by direct esterification of terephthalic acid (TPA) with linear glycols, such as ethylene glycol (2G), 1,3-propanediol (3G) and 1,4-butanediol (4G), are well known in the art. Continuous processes for preparing polyethylene terephthalate (2GT) at commercially acceptable throughputs can be carried out to high TPA conversion without the use of an esterification catalyst by performing the reaction at sufficiently high temperatures, typically greater than 270° C. Increasing the reaction temperature typically acts to accelerate the reaction of TPA and thereby improve throughput. Unfortunately, 3G and polytrimethylene terephthalate (3GT) are thermally unstable at high temperatures. Operation of a continuous process for preparing 3GT at such temperatures would generate harmful byproducts, such as acrolein and allyl alcohol, and lead to poor polymer quality.

TPA-based routes to 3GT polymer suffer disadvantages relative to routes based on use of terephthalate esters due to the low solubility of TPA in 3G, which retards its reaction, and, in a continuous process, insufficient reaction of TPA results in carryover of unreacted TPA into downstream equipment. The presence of unreacted TPA in downstream equipment can cause operability problems such as TPA deposits creating flow problems. The presence of TPA in finished polymer results in processing problems, such as poor filterability and spinning problems.

U.S. Pat. No. 4,680,376 discloses a process for continuous production of high molecular weight polybutyleneterephthalate by direct esterification of TPA and 4G in the presence of tin- or titanium-containing catalysts.

U.S. Pat. Nos. 6,277,947 and 6,326,456 disclose a process for preparing 3GT by esterification of TPA with trimethylene glycol in the presence of a catalytic titanium compound, precondensation and polycondensation. The esterification is effected in at least 2 stages.

However, there is no commercial process for continuously producing 3GT using TPA. It is highly desirable to develop a contiguous process, especially a low temperature process for esterifying TPA with 3G, that can minimize the generation of harmful byproducts disclosed above and provide TPA reaction rates to maintain commercially attractive throughputs. It is also highly desirable to develop a contiguous process that uses low quantities of catalyst and is capable of operating at total residence times in the esterifier of less than 4 hours to minimize discoloration and improve polymer quality. It is further desirable to develop a process for producing 3GT by a continuous esterification of TPA with 3G to produce an oligomer and using the oligomer for polymerization to high molecular weight 3GT polymer that does not exhibit filterability problems during spinning.

SUMMARY OF THE INVENTION

This invention provides a process that can be used for direct esterification of a dicarboxylic acid such as terephthalic acid with a glycol such as 1,3-propanediol. The process comprises (1) contacting, at an elevated temperature, optionally in the presence of a preformed oligomer, the acid with the glycol to produce a product mixture comprising (i) a water vapor mixture comprising water and volatile glycol, which or a portion of which exits the product mixture at the elevated temperature to form a water-glycol vapor and (ii) liquid product mixture comprising free glycol and an oligomer having a degree of polymerization of from about 1.9 to about 3.5 and comprising repeat units derived from the acid; optionally (2) separating the glycol in the water-glycol vapor from the water-glycol vapor to produce a recovered glycol; optionally (3) returning the recovered glycol to the product mixture to maintain the oligomer's degree of polymerization in the range of about 1.9 to about 3.5; and optionally (4) recovering the liquid product mixture. Steps (1) to (4) can be continuously repeated for as long a period as one skilled in the art deems appropriate.

DETAILED DESCRIPTION

The present invention provides a process for direct esterification of a dicarboxylic acid and a glycol to produce an oligomer comprising repeat units derived from the acid and the glycol. It is preferred that the process be carried out in a single stage, such as, for example, with or in a single esterifier. The oligomer can be subsequently used for producing a polymer, such as polyester, comprising repeat units derived from the acid and the glycol.

The term "oligomer" refers to a polymer having a degree of polymerization ($DP_n$) from about 1.5 to about 10, or about 1.5 to about 10 repeat units of a monomer or monomers. The preferred oligomer has a degree of polymerization ($DP_n$) in the range of from, preferably about 1.9 to about 3.5 and more preferably 1.9 to 3.5.

The term "free glycol" means, unless otherwise indicated, unreacted glycol in the liquid product mixture that is not chemically bound to an oligomer or acid through an ester or ether linkage. The term "glycol" used herein is exchangeable with "diol". The term "excess free glycol" refers to the concentration of free glycol present in the liquid product mixture in the range of from about 1 to about 25, preferably 1 to 20, and more preferably 3 to 15 weight %, based on the total weight of the acid and glycol.

An oligomer having a $DP_n$ in this range can be obtained by, as disclosed below, maintaining desired levels of excess glycol in the liquid product mixture. The excess glycol levels can be obtained by, for example, refluxing back into the product mixture glycol that had volatized from the product mixture or by increasing the pressure thereby decreasing the volatility of glycol from the product mixture or by a combination of, for example, reflux and pressure.

The term "elevated temperature" denotes a temperature in the range of from about 220° C. to about 260° C., preferably about 225° C. to about 260° C., and most preferably 235° C. to 255° C.

Terephthalic acid (TPA) is the preferred acid for producing an oligomer. Other dicarboxylic acids, individually or in combination, may also be used. For example, as high as 15 mole %, in a polymer produced from the oligomer, of an acid other than TPA may be used together with TPA. The other dicarboxylic acids that may be used include, but are not limited to, linear, cyclic, and branched aliphatic dicarboxylic acids having 4 to 12 carbon atoms; aromatic dicarboxylic acids other than terephthalic acid and having about 8 to about 14 carbon atoms; and combinations of two or more thereof.

Examples of suitable other dicarboxylic acids include, but are not limited to, butanedioic acid, pentanedioic acid, hexanedioic acid, dodecanedioic acid, 1,4-cyclohexanedicarboxylic acid, isophthalic acid, 2,6-naphthalenedicarboxylic acid, and combinations of two or more thereof. Isophthalic acid, pentanedioic acid, hexanedioic acid, or combinations of two or more thereof are preferred other dicarboxylic acids because they are readily available from commercial sources and inexpensive.

The preferred glycol is 1,3-propanediol (3G). Other glycols, individually or in combination, may also be used. For example, as high as 15 mole %, in a polymer produced from the oligomer, of a glycol other than 3G may be used together with 3G. Other glycols that may be used include, but are not limited to, linear, cyclic, and branched aliphatic diols having 3–8 carbon atoms; aliphatic and aromatic ether glycols having about 4 to about 20, preferably 4 to 10, carbon atoms; and combinations of two or more thereof.

Examples of suitable other glycols include, but are not limited to, 1,2-propanediol, 1,4-butanediol, 3-methyl-1,5-pentanediol, 2,2-dimethyl-1,3-propanediol, 2-methyl-1,3-propanediol, and 1,4-cyclohexanediol, hydroquinone bis(2-hydroxyethyl)ether, poly(ethylene ether) glycol having a molecular weight below about 460, diethylene ether glycol, and combinations of two or more thereof. The preferred other glycol is 1,4-butanediol because it is readily available from commercial sources and inexpensive.

Other comonomers may also be used. Such other comonomers include 5-sodium-sulfoisophthalate, in an amount from about 0.01 to about 5 mole %. Small amounts of trifunctional comonomers, for example, trimellitic acid, may be used for viscosity control.

The process may also be carried out in the presence of a catalytic amount of a catalyst. Catalysts useful in the process of the invention include, but are not limited to, organic and inorganic compounds of titanium, tin, lanthanum, zinc, copper, magnesium, calcium, manganese, iron and cobalt, and combinations of two or more thereof such as their oxides, carbonates, phosphorus derivatives, and alkyl, aryl and aryl derivatives. Examples of such catalysts include, but are not limited to, tetraisopropyl titanate, tetraisobutyl titanate, lanthanum acetylacetonate and cobalt acetate. Organic titanium and organic zirconium compounds such as those disclosed in U.S. Pat. Nos. 3,056,818; 3,326,965; 5,981,690; and 6,043,335 are suitable for use here. Examples of tin catalysts including n-butylstannoic acid, octylstannoic acid, and others as described in U.S. Pat. No. 6,281,325 may also be used. The disclosures of these patents are incorporated herein by reference. Titanium catalysts, such as tetraisopropyl titanate and tetraisobutyl titanate are preferred. In addition, a mixed titanium/zirconium catalyst may be alternatively preferred wherein the catalyst is prepared from (a) tetraalkyl titanate, (b) tetraalkyl zirconate, and (c) tetraalkyl ammonium hydroxide, as disclosed in co-owned, pending U.S. Patent Application Ser. No. 60/398675, filed Jul. 26, 2002, the teachings of which are incorporated herein by reference.

Generally a catalyst in an amount sufficient to yield about 5 to about 200 ppm (parts per million by weight), preferably 10 to 100 ppm, as metal weight based on weight of final polymer such as, for example, poly(1,3-propylene terephthalate), formed in subsequent process using the oligomer, may be used.

The contacting of acid and glycol can be carried out in any suitable esterification vessels such as an "esterifier", either batch wise, semi-continuously, or continuously. Because such esterification vessel is well known to one skilled in the art, the description of which is omitted for the interest of brevity. Such vessel is referred to herein below as "reactor".

Continuous process is preferred. Any continuous process such as, for example, continuous stirred tank reactor and plug flow reactor, can be used to continuously introduce acid, glycol, and any other feeds to a reactor. The oligomer-containing product can be continuously withdrawn.

The acid, glycol, catalyst, any other acid, any other glycol, and comonomer, can be separately, or combined as a premixed feed which is then delivered to a reactor. For example, 3G, TPA, and catalyst may be pre-mixed and fed to a reactor. Some heating may occur during mixing, raising the temperature, for example, to about 60° C., prior to feeding. Optionally, the premixed feed may be advantageously preheated, for example, to a temperature up to about 200° C. Depending on relative concentrations and temperature, this mixture may be fed as a slurry.

The mole ratio of glycol:acid may be in the range of from 1 to 10, preferably 1 to 3, excluding the recovered glycol that is returned to the product mixture.

Control of the free glycol levels in the product mixture comprising the oligomer may affect the reaction rate. Generally, higher free glycol concentration in the product mixture increases the solubility of acid and reaction rate. The lower the free glycol levels, the lower the acid solubility and, consequently, the throughput.

In controlling the concentration of free glycol in the liquid product mixture, the maintenance of high levels of free 3G can be monitored by $DP_n$ of the oligomer in the vessel where $DP_n$ is inversely related to the level of free glycol. As disclosed above, for acceptably high free glycol levels, the oligomer preferably has a low $DP_n$ of from about 1.9 to about 3.5, preferably 1.9 to 3.5.

Generally, as an esterification process proceeds, water is produced. Glycol vapor is carried with the water vapor that exits the reactor or the product mixture thereby depleting the free glycol level in the product mixture. That is, there can be little free glycol remaining in the liquid product mixture.

According to the invention, the glycol in the water/glycol vapor mixture exiting the reactor or liquid product mixture is separated and recovered by, for example, passing the exiting water-glycol vapor mixture through a cooling means such as, for example, a condenser under a temperature that selectively condenses the glycol to glycol condensates that can be returned to the product mixture or reactor whereas the water continues to exit, generally as vapor, leaving the product mixture or reactor. The recovered glycol is returned to the product at a rate sufficient to maintain the desired concentration of free glycol in the liquid product mixture disclosed above. The liquid product mixture also comprises an oligomer as disclosed above. Any temperature that can selectively condense a glycol can be used. Generally, such temperature is dependent on the type of glycol used and can be a temperature below the boiling point of the glycol. For example, a temperature in the range of from about 100° C. at the exiting point of the exiting water vapor mixture to about 200° C. at the entering point of the exiting water-glycol vapor mixture can be used. Other cooling or condensing means known to one skilled in the art may also be used. Because such condensing means are well known to one skilled in the art, the description of which is omitted herein.

According to the invention, the desired free glycol concentration in the product mixture may be determined by monitoring the $DP_n$ of the oligomer produced. The free glycol concentration disclosed above is merely a guide to one skilled in the art. $DP_n$, increases as free glycol concentration decreases. Generally, if $DP_n$, increases to an undesirably high (i.e., much higher than the range disclosed above), solubility of acid and acid conversion (to an oligomer), in the reactor decreases. On the other hand, if $DP_n$, decreases to undesirably low levels (i.e., much lower than the range disclosed above), excess glycol may be carried through the process resulting in additional demands downstream, such as on precondensation vessels.

The invention process is preferably carried out at the temperature disclosed above, which is "low" compared to known commercial esterification processes utilizing the same reactors. As disclosed above, the process may be carried out under a suitable pressure to maintain the $DP_n$ in the desired range. For example, a pressure from about 100 to 600 kPa, preferably 100 to 500 kPa, and more preferably 100 to 400 kPa, may be employed.

Also, carrying out the process under elevated pressure can increase the free glycol concentration in the liquid product mixture thereby reducing the need for condensing and returning the condensed glycol to the product mixture.

The liquid product mixture is withdrawn from the reactor. The liquid product mixture may contain a small quantity of water, a small quantity of unreacted acid, and free glycol.

The steps for producing an oligomer disclosed above can be repeated for as long as one skilled in the art desires by a contiguous process disclosed above under which acid and glycol feeds are continuously fed to a reactor and the oligomer is continuously withdrawn from the reactor.

The oligomer in the liquid product mixture such as, for example, 3GT oligomer, may be used for subsequent polycondensation, optionally in the presence of a catalyst disclosed above, to a high molecular weight polymer such as 3GT polymer. The polycondensation means are known to one skilled in the art. Such polymer produced from the oligomer disclosed herein has improved filterability and reduced pack pressure problems during spinning into fibers.

For example, using TPA and 3G as feeds, a low molecular weight oligomer of 3GT is produced. This oligomer may advantageously have a carboxyl level of less than 400 meq/kg, preferably less than 300 meq/kg and is suitable for further polymerization into high molecular weight 3GT polymer. The oligomer can be fed into a flasher, prepolymerizer and finisher to continuously produce a polymer with an IV up to 1.1. Alternatively, the 3GT oligomer may be fed into a single prepolymerizer and a finisher to produce a polymer with an IV up to 1.1. Catalyst and other additives, such as delusterants, color agents, branching agents, stabilizers, viscosity boosters, pigments, antioxidants, or combinations thereof, generally up to about 200 ppm may be added to the oligomer prior to entering the flasher or prepolymerizer.

EXAMPLES

The following examples are provided to illustrate the invention and should not be construed as to unduly limit the scope of the invention.

Example 1

A round-bottomed, stirred reaction flask containing 300 cc of a starting low molecular weight 3GT oligomer ($DP_n$= 4.3), 2,1 weight % free 3G, and 50 ppm Ti catalyst in the form of tetraisopropyltitanate (Tyzor® TPT, available from E. I. du Pont de Nemours and Company, Wilmington Del.; hereinafter referred to as TPT catalyst) was outfitted with an overflow port and a 6 inch (15.24 cm) air-cooled column for collecting $H_2O$ and excess 3G distillate. The oligomer was heated to 250° C. while bubbling 200 cc /min $N_2$ into the liquid to exclude air from the reactor. After reaching 250° C., $N_2$ flow was discontinued and 70.3 g/h of TPA and 56.3 g/h of 3G (3G/TPA mole ratio=1.75) was injected. Tyzor® TPT catalyst was added hourly to maintain an average catalyst level of 50 ppm Ti (relative to final polymer). In the first 2.5 hours, the average oligomer production rate through the overflow port steadied to approximately 98 g/h. At 2.5 hours, the flows of TPA and 3G were suddenly stopped and the oligomer was observed to clear of all small bubbles (i.e., $H_2O$ generation from esterification had slowed appreciably) after approximately 3.4 minutes. Samples of the oligomer from the overflow port were collected by quenching in liquid nitrogen and analyzed by NMR.

For analysis, oligomer samples were dissolved in 1,1,2,-tetrachloroethane-d2 and analyzed by $H^1$ NMR at 50° C. in a Bruker 500 MHz instrument, averaged over 64 scans. Analysis at 50° C. provides sufficient resolution of the terminal methylene hydrogen triplet of unreacted or free 3G (3.81 ppm) from the terminal methylene triplet of a propoxyl end group (3.77 ppm). Integration of these areas and areas representative of terephthalate, cyclic dimer, internal ester and dipropylene glycol groups enables calculation of free 3G levels and the number averaged degree of polymerization, $DP_n$. NMR analysis showed the oligomer to contain approximately 7.5 weight % free 3G or have a $DP_n$ of 2.6. Conversion of TPA was estimated at 96%. Due to chemical and thermodynamic equilibrium, it is known that free 3G levels are inversely proportional to $DP_n$ at a given reaction temperature. Thus, operating temperature and $DP_n$ are sufficient to determine free 3G levels and vice versa. Parameters and results are provided in Table 1.

Comparative Example A

Using the same oligomer and reactor configuration as remaining at the end of Example 1, the 6 inch (32.4 cm) column was replaced by a one inch (2.54 cm) column. In addition, 200 cc/min $N_2$ was injected into the reactor at the same time as a feed of 70.3 g/h TPA and 56.3 g/h 3G was started. The nitrogen gas facilitated the exit of glycol from the reactor thereby decreasing the free 3G levels in the reactor. Reactor temperature was maintained at 250° C. TPT catalyst was added hourly to maintain an average catalyst level of 50 ppm Ti (relative to final polymer). After 1 hour of operation, only 54 g/h of oligomer was collected indicating a buildup of TPA inside the reactor. In the next 30 minutes, only 67 g/h of oligomer was collected, again, less than the feed rate of TPA. Flow of TPA, 3G and $N_2$ were all discontinued after 1.5 h of this test. Bubbling within the oligomer continued for approximately 9 minutes, reflecting the additional time required for the unconverted TPA, that had accumulated over 1.5 h, to dissolve and subsequently esterify. NMR analysis of the oligomer collected after 1.5 hours showed it to have a $DP_n$ of 3.8 and contain only 3.1 weight % free 3G. Thus, the higher $DP_n$, (or lower free 3G level) of the oligomer decreased the esterifier throughput capacity, resulting in non-uniform oligomer production rates and hence, buildup of TPA within the reactor. This example demonstrates that despite the same feed rates, catalyst, and temperature as in Example 1, lower free 3G levels in the oligomer lead to poor TPA conversion and hence, unstable operation. Conversion of TPA was less than 94%.

Example 2

Approximately 25 g of 3G was added to the oligomer remaining in the reactor at the end of Comparative Example A. With the 2.54 cm column installed and the temperature steady at 250° C., a feed containing 70.3 g/h TPA and 56.3 g/h 3G was injected, together with $N_2$ at 50 cc/min. After 1 hour of operation, oligomer production stabilized at approximately 95 g/h. TPT catalyst was added hourly to maintain an average catalyst level of 50 ppm Ti (relative to final polymer). After 3 hours, all feeds were stopped and the oligomer was observed to be clear of small bubbles after 5.5 minutes. NMR analysis of the oligomer indicated the $DP_n$, to be 3.3 and free 3G level to be approximately 4.1%.

Example 3

An oligomer (300 cc) was heated to 250° C. in a reactor equipped with a 1 inch (2.54 cm) column. The reactor was purged with $N_2$ during heat-up, but no $N_2$ was added when injecting 70.3 g/h TPA and 56.3 g/h 3G. TPA and 3G were injected continuously for 9 hours (TPT was added to maintain a catalyst level of 50 ppm Ti) with no apparent accumulation of TPA in the reactor. After stopping all feeds, the oligomer was observed to clear of small bubbles after 3–4 minutes. The average oligomer production rate was approximately 102 g/h and NMR analysis of the oligomer showed the $DP_n$, to be approximately 2.8 and the free 3G level to be 4.7–5.3 weight %.

Example 4

An oligomer (300 cc) was heated to 250° C. in a reactor equipped with a 6 inch (15.24 cm) column. The reactor was purged with $N_2$ during heat-up, but no $N_2$ was added when injecting 70.3 g/h TPA and 56.3 g/h 3G. TPA and 3G were injected continuously for 9 hours (TPT was added to maintain a catalyst level of 50 ppm Ti) with no apparent accumulation of TPA in the reactor. After stopping all feeds, the oligomer was observed to clear of small bubbles after about 3 minutes. The average oligomer production rate was 120 g/h and NMR analysis of the oligomer showed the $DP_n$, to be approximately 2.3 and the free 3G level to be 7.2–8.3 weight %. The higher level of reflux associated with the longer $H_2O$ distillation column resulted in higher levels of free 3G in the oligomer and thus, lower oligomer $DP_n$.

Example 5

An oligomer (300 cc) was heated to 240° C. in a reactor equipped with a 6 inch (15.24 cm) column. The reactor was purged with $N_2$ during heat-up, but no $N_2$ was added when injecting 70.3 g/h TPA and 62.7 g/h 3G. TPA and 3G were injected continuously for 8 hours (TPT was added to maintain a catalyst level of 50 ppm Ti) with no apparent accumulation of TPA in the reactor. The average oligomer production rate was approximately 111 g/h and NMR analysis of the oligomer showed the $DP_n$, to be approximately 2.0 and the free 3G level to be 9.8–11.0 weight %.

Example 6

With the equipment and procedure in Example 5, 83.0 g/h TPA and 76.0 g/h 3G were injected at 240° C. into the oligomer continuously for 8 hours (TPT was added to maintain a catalyst level of 50 ppm Ti) with no evident operational problems. The average $DP_n$ of the oligomer was 1.98 and the free 3G level was approximately 10.7 weight %. Although TPA throughput is increased by almost 20% over Example 5, the high free 3G level of the oligomer is able to accommodate the increased feed with an approximate holdup time of 3 hours. Moreover, the lower temperatures and holdup times below 4 hours are favorable for processing thermally sensitive 3GT.

Example 7

An self-circulating esterifier designed after U.S. Pat. No. 3,927,982 was filled with 3GT oligomer, pressurized to 25 psig (about 274 KPa) and heated to 245° C. A paste containing 3G and TPA at a mole ratio of about 2.2 (48.3 lb/h (22 kg/h) TPA and 48.7 lb/h (22.1 kg/h) 3G), and TPT at a level of 50 ppm Ti (relative to final polymer) was continually injected into the reactor at a polymer production rate of 60 lb/h (27.3 kg/h) for over 1 day. $H_2O$ and 3G vapors were continually extracted into a distillation column where $H_2O$ and byproducts were separated from 3G. The 3G condensed from the distillation column was recycled for use in making the TPA/3G paste. Oligomer from the esterifier was continually withdrawn and an additional 30 ppm Ti (in the form of TPT) was injected into the oligomer before it was passed through 2 precondensation vessels and a finisher. Processing of the oligomer was accomplished after the method described in WO 01/58981A1 to produce 3GT polymer with intrinsic viscosities between 0.60 and 0.95 dl/g. NMR analysis of a typical oligomer indicated the $DP_n$ to be approximately 2.9.

Example 8

After 1 day of continuous polymer production at 60 lb/h (27.3 kg/h) capacity as described in Example 7, 3GT production was increased to approximately 80 lb/h; (36.4 kg/h; TPA feed to the esterifier of 64.4 lb/h (29.3 kg/h) and 3G/TPA mole ratio of about 2.2). All catalyst levels and conditions were the same as in Example 7. The 80 lb/h (36.4 kg/h) production rate was maintained for approximately 2 days with IV's of 3GT polymers ranging between 0.80 and 0.98 dl/g. NMR analysis of oligomer indicated a $DP_n$ of 3.1.

Comparative Example B

The example was similarly carried out as disclosed in Example 7 except that the feed paste contained about 50 lb/h (22.7 kg/h) TPA and 3G (molar ratio 2.1), the temperature was 244° C., the esterifier was operated at atmospheric pressure, and 3G vapors condensed from the column were collected in a recycle tank from which 3G was refluxed back into the vapor space of the esterification reactor at a rate of about 47 lb/h (21.4 kg/h; 2.1 3G/TPA mole ratio). Including reflux, the total molar 3G /TPA feed to the reactor was 4.2. TPT catalyst was initially added to the paste at a rate equivalent to 50 ppm Ti relative to final polymer. Oligomer exiting the esterification reactor was sampled approximately every 4 hours into a sealed cylinder.

To analyze for residual carboxyl ends, oligomer samples were dissolved in heated o-cresol. Residual carboxyl ends were then measured by titration using a 0.005 N KOH in methanol solution. During the following 2 days of operation, oligomer carboxyl ends were observed to increase to above 400 meq/kg while oligomer $DP_n$ increased as high as 4.0. Operational problems such as, for example, plugged lines and pumps, were encountered due to the presence of unreacted TPA in downstream equipment necessitating maintenance and discontinuation of flow into downstream reaction vessels until the unreacted TPA could be cleared.

Comparative Example C

After injecting 3G into the esterifier oligomer as described in Comparative Example B, residual carboxyl levels decreased to about 224 meq/kg and the oligomer was visually observed to be clear of unreacted TPA. Paste containing about 50 lb/h (22.7 kg/h) TPA, 48 lb/h (21.8 kg/h)

3G and 50 ppm Ti (based on final polymer) was continuously injected into the esterifier. 3G condensed from the esterifier column was refluxed into the top of the reactor at a rate of about 83 lb/h (37.7 kg/h; total molar 3G/TPA feed of 5.7). The oligomer temperature was held at 244° C. and the esterifier was operated at atmospheric pressure. Carboxyl levels rose slowly over the next 2 days to above 400 meq/kg as the oligomer $DP_n$, slowly rose above 3.2. The rising carboxyl levels and increasing oligomer $DP_n$, were consistent with visual observations of undesirably high levels of unconverted TPA in the oligomer.

Example 9

The esterifier in Comparative Example C was injected with 3G until carboxyl levels decreased to 100 meq/kg and oligomer was visually observed to be clear of unreacted TPA. Paste containing about 50 lb/h (22.7 kg/h) TPA, 48 lb/h (21.8 kg/h) 3G, and 50 ppm Ti (based on final polymer) was continuously injected into the esterifier. 3G condensed from the esterifier column was refluxed into the top of the reactor at a rate of about 97 lb/h (44.1 kg/h; total molar 3G/TPA feed of 6.3). The oligomer temperature was held at 244° C. and the esterifier was operated at atmospheric pressure. With the higher level of 3G reflux, oligomer $DP_n$, remained stable at about 2.9 and oligomer carboxyl levels remained stable at approximately 75 meq/kg.

A stream containing 30 ppm Ti (weight based on final polymer; TPT mixed in 3G) was added to the oligomer and polymerized in accordance with WO 01/58981A1 to produce 3GT polymers with IV's between 0.8 and 1 dl/g.

Example 10

With the same conditions in Example 9, the TPT catalyst level injected with the paste was reduced to 30 ppm Ti (based on final polymer). Oligomer carboxyl levels rose and began to stabilize after 1 day to about 140 meq/kg. Oligomer $DP_n$ was about 3.0. TPT catalyst (30 ppm Ti) was added to the oligomer, which was then polymerized to produce 3GT polymers with IV's between 0.9 and 1 dl/g.

What is claimed is:

1. A process comprising contacting, at an elevated temperature, a dicarboxylic acid with a glycol to produce a product mixture comprising (i) a water vapor mixture comprising water and volatile glycol, said water vapor mixture or a portion thereof exits said product mixture to form a water-glycol vapor and (ii) liquid product mixture comprising free glycol and an oligomer having a degree of polymerization of from about 1.9 to about 3.5 and comprising repeat units derived from the acid.

2. A process according to claim 1 further comprising separating said glycol in said water-glycol vapor from said water-glycol vapor to produce a recovered glycol; and combining said recovered glycol and said liquid product mixture thereby maintaining the degree of polymerization of said oligomer in the range of from about 1.9 to about 3.5.

3. A process according to claim 2 wherein said acid is terephthalic acid and said glycol is 1,3-propanediol; said process further comprises recovering said liquid product mixture; and said contacting, said separating, said combining, and said recovering are continuously repeated.

4. A process according to claim 2 wherein said liquid product mixture comprises about 1 to about 20 weight % free glycol based on the weight of said liquid product mixture.

5. A process according to claim 3 wherein said liquid product mixture comprises 3 to 15 weight % free glycol based on the weight of said liquid product mixture.

6. A process according to claim 5 wherein said temperature is in the range of from about 235° C. to about 255° C.

7. A process according to claim 1 wherein said process is carried out under a pressure in the range of from about 100 to about 500 KPa.

8. A process according to claim 1 wherein said process is carried in one stage.

9. A process according to claim 7 wherein said process is carried in one stage.

10. A process according to claim 6 wherein said process is carried in one stage and said separating is carried out by passing said water-glycol vapor through a condenser.

11. A process according to claim 10 wherein said process is carried out in the presence of a preexisting oligomer comprising repeat units derived from said terephthalic acid and said 1,3-propanediol.

12. A process according to claim 3 further comprising polymerizing said liquid product mixture under a polycondensation condition to produce poly(trimethylene terephthalate).

13. A process according to claim 7 further comprising polymerizing said liquid product mixture under a polycondensation condition to produce poly(trimethylene terephthalate).

14. A process according to claim 11 further comprising polymerizing said liquid product mixture under a polycondensation condition to produce poly(trimethylene terephthalate).

15. A process comprising (1) continuously contacting, at about 220 to about 260° C. terephthalic acid with 1,3-propanediol to produce a product mixture comprising (i) a water vapor mixture comprising vapor of said 1,3-propanediol, said water vapor mixture or a portion thereof exits said product mixture to form an water-glycol vapor and (ii) a liquid product mixture comprising free 1,3-propanediol and an oligomer having a degree of polymerization of from 1.9 to 3.5 and comprising repeat units derived from said terephthalic acid and 1,3-propanediol; (2) separating said 1,3-propanediol in said water-glycol vapor from said water-glycol vapor to produce a recovered 1,3-propanediol; and (3) returning said recovered 1,3-propanediol to said liquid product mixture such that said liquid product mixture comprises 1 to 20 weight % free 1,3-propanediol based on the weight of said liquid product mixture.

16. A process according to claim 15 wherein said liquid product mixture comprises 3.5 to about 15 wieght % free 1,3-propanediol.

17. A process according to claim 16 wherein said process is carried in one stage.

18. A process according to claim 17 wherein said process further comprises polymerizing said liquid product mixture under a polycondensation condition to produce poly(trimethylene terephthalate).

19. A continuous process for esterifying terephthalic acid with 1,3-propanediol comprising (1) contacting, at a temperature of about 235° C. to about 255° C., said terephthalic acid, in a single stage esterifier, with 1,3-propanediol sufficient to convert at least 95% of said terephthalic acid to produce a product mixture comprising (i) a water vapor mixture comprising 1,3-propanediol vapor and (ii) a liquid product mixture comprising an oligomer comprising repeat units derived from said terephthalic acid and said 1,3-propanediol and has a degree of polymerization of from 1.9 to 3.5 ; (2) passing said water vapor mixture through a cooling means under a temperature that produces 1,3-propanediol condensate; (3) returning said 1,3-propanediol condensate to said liquid product mixture such that said liquid product mixture comprises 1 to 20 weight % free 1,3-propanediol based on said liquid product mixture; and optionally (3) recovering said liquid product mixture.

20. A process according to claim 19 wherein said liquid product mixture comprises 3 to 15 weight % free 1,3-propanediol and said oligomer.

21. A process according to claim 20 further comprising polymerizing said liquid product mixture under a polycondensation condition to produce poly(trimethylene terephthalate).

22. A continuous process for esterifying terephthalic acid with 1,3-propanediol comprising contacting, under a pressure in the range of from 100 to 400 KPa, said terephthalic acid, in a single stage esterifier, with 1,3-propanediol sufficient to convert at least 95% of said terephthalic acid to produce a product mixture comprising (i) a water vapor mixture comprising unreacted 1,3-propanediol mixture and (ii) a liquid product mixture comprising an oligomer comprising repeat units derived from said terephthalic acid and said 1,3-propanediol and has a degree of polymerization of from 1.9 to 3.5.

23. A process according to claim 22 further comprising recovering said liquid product mixture and polymerizing said liquid product mixture under a polycondensation condition effective to produce poly(trimethylene terephthalate).

24. A process according to claim 22 further comprising separating said 1,3-propanediol in said water-glycol vapor from said water-glycol vapor to produce a recovered 1,3-propanediol; returning said recovered 1,3-propanediol to said liquid product mixture such that said liquid product mixture comprises 1 to 20 weight % free 1,3-propanediol based on the weight of said liquid product mixture; recovering said liquid product mixture; and polymerizing said liquid product mixture under a polycondensation condition effective to produce poly(trimethylene terephthalate).

* * * * *

UNITED STATES PATENT AND TRADEMARK OFFICE
CERTIFICATE OF CORRECTION

PATENT NO. : 6,887,953 B2
APPLICATION NO. : 10/269734
DATED : May 3, 2005
INVENTOR(S) : Eng John Harvey It is certified that error appears in the above-identified patent and that said Letters Patent is hereby corrected as shown below:

In column 1, line 50, "3GT using TPA." should read --3GT using TPA in a single stage esterifier--

In column 1, line 51, "to develop a contiguous process" should read --to develop a continuous process--

In column 1, line 55, "to develop a contiguous process" should read --to develop a continuous process--

In column 5, line 29, "a contiguous process disclosed" should read -- a continuous process disclosed--

In column 2, line 34, please delete "and more preferably 1.9 to 3.5."

In column 3, line 42, "tetraisopropyl titanate, tetraisobutyl titanate" should read --tetrabutyl titanate, tetrabutyl titanate--

In column 3, line 51, "such as tetraisopropyl titanate and tetraisobutyl titanate" should read --such as tetrabutyl titanate and tetrabutyl titanate--

In column 6, line 17, "For analysis, oligomer samples were dissolved in 1,1,2,-" should read --For analysis, oligomer samples were dissolved in 1.1,2,2- --

In column 9, line 53, in claim 2, "and said liquid product" should read --and said product--

In column 10, line 41, in claim 15, "to said liquid product mixture such that" should read --to said product mixture such that--

In column 10, line 46, in claim 16, "to about 15 wieght" should read --to about 15 weight--

In column 10, line 67, in claim 19, "to said liquid product mixture" should read --to said product mixture--

UNITED STATES PATENT AND TRADEMARK OFFICE
CERTIFICATE OF CORRECTION

PATENT NO. : 6,887,953 B2
APPLICATION NO. : 10/269734
DATED : May 3, 2005
INVENTOR(S) : Eng John Harvey It is certified that error appears in the above-identified patent and that said Letters Patent is hereby corrected as shown below:

In column 12, line11, in claim 24, "to said liquid product mixture" should read --to said product mixture--

Signed and Sealed this

Twenty-second Day of August, 2006

JON W. DUDAS
*Director of the United States Patent and Trademark Office*